(12) United States Patent
Ahmed

(10) Patent No.: US 12,360,523 B2
(45) Date of Patent: Jul. 15, 2025

(54) SYSTEMS, APPARATUS, AND METHODS OF ANALYZING SPECIMENS

(71) Applicant: Siemens Healthcare Diagnostics Inc., Tarrytown, NY (US)

(72) Inventor: Muhammad Ahmed, Yonkers, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 565 days.

(21) Appl. No.: 17/755,641

(22) PCT Filed: Oct. 29, 2020

(86) PCT No.: PCT/US2020/057909
§ 371 (c)(1),
(2) Date: May 4, 2022

(87) PCT Pub. No.: WO2021/091755
PCT Pub. Date: May 14, 2021

(65) Prior Publication Data
US 2022/0390936 A1    Dec. 8, 2022

Related U.S. Application Data

(60) Provisional application No. 62/931,113, filed on Nov. 5, 2019.

(51) Int. Cl.
*G05B 23/02* (2006.01)
*G06V 20/69* (2022.01)
(Continued)

(52) U.S. Cl.
CPC ....... *G05B 23/0275* (2013.01); *G06V 20/695* (2022.01); *G16H 30/40* (2018.01); *G16H 40/67* (2018.01)

(58) Field of Classification Search
CPC ............. G05B 23/0275; G06V 20/695; G06V 20/698; G16H 30/40; G16H 40/67; G16H 40/20
See application file for complete search history.

(56) References Cited

U.S. PATENT DOCUMENTS

| 6,055,487 A | 4/2000 | Margery et al. |
| 6,230,043 B1 | 5/2001 | Johnson |

(Continued)

FOREIGN PATENT DOCUMENTS

| EP | 2389573 B1 | 1/2016 |
| JP | 2000305804 A | 11/2000 |

(Continued)

OTHER PUBLICATIONS

Extended EP Search Report dated Nov. 25, 2022 of corresponding European Application No. 20885690.6, 5 Pages.

(Continued)

*Primary Examiner* — Siamak Harandi

(57) ABSTRACT

A method of analyzing a specimen includes detecting a specimen integrity error in the specimen; capturing an image of the specimen; sending the image of the specimen to a customer support center at a remote location; analyzing the image of the specimen at the customer support center; and determining a cause of the specimen integrity error in response to analyzing the image of the specimen. Diagnostic analyzers and diagnostic systems are also disclosed.

20 Claims, 6 Drawing Sheets

(51) Int. Cl.
  *G16H 30/40* (2018.01)
  *G16H 40/67* (2018.01)

(56) References Cited

U.S. PATENT DOCUMENTS

| | | | |
|---|---|---|---|
| 6,735,597 B1 | 5/2004 | Paradies | |
| 7,359,536 B2 | 4/2008 | Hays et al. | |
| 7,634,367 B1 | 12/2009 | Ding et al. | |
| 8,059,001 B2 | 11/2011 | Parvin et al. | |
| 8,099,257 B2 | 1/2012 | Parvin et al. | |
| 9,483,441 B2 | 11/2016 | Li et al. | |
| 9,915,674 B2 | 3/2018 | Zordan | |
| 10,267,813 B1 | 4/2019 | Bhatia et al. | |
| 10,395,357 B2 | 8/2019 | Vivet et al. | |
| 2002/0165673 A1* | 11/2002 | Morgan | A61B 10/0096 702/19 |
| 2007/0003112 A1 | 1/2007 | Awatsu et al. | |
| 2007/0143063 A1 | 6/2007 | Kaplit | |
| 2008/0305012 A1* | 12/2008 | Camenisch | G01N 35/1016 422/400 |
| 2009/0074273 A1 | 3/2009 | Fischer et al. | |
| 2010/0135552 A1 | 6/2010 | Leib et al. | |
| 2013/0151189 A1 | 6/2013 | Li et al. | |
| 2016/0291049 A1* | 10/2016 | Arumugam | G01N 35/0099 |
| 2017/0370956 A1 | 12/2017 | Hurwitz et al. | |
| 2019/0033209 A1 | 1/2019 | Kluckner et al. | |
| 2019/0033230 A1 | 1/2019 | Kluckner et al. | |

FOREIGN PATENT DOCUMENTS

| | | |
|---|---|---|
| JP | 2012-008077 A | 1/2012 |
| JP | 2019-504996 A | 2/2019 |
| WO | 2012/100235 A2 | 7/2012 |
| WO | 2015/066342 A1 | 5/2015 |
| WO | 2019/188599 A1 | 10/2019 |

OTHER PUBLICATIONS

PCT International Search Report and Written Opinion dated Mar. 12, 2021 (10 Pages).

* cited by examiner

SYSTEMS, APPARATUS, AND METHODS OF ANALYZING SPECIMENS

CROSS REFERENCE TO RELATED APPLICATION APPLICATIONS

This disclosure is a 371 of PCT/US2020/057909, filed Oct. 29, 2020, which claims the benefit of U.S. Provisional Patent Application No. 62/931,113, entitled "SYSTEMS, APPARATUS, AND METHODS OF ANALYZING SPECIMENS," filed Nov. 5, 2019, the disclosures of which is are hereby incorporated by reference in their entireties for all purposes.

FIELD

Embodiments of this disclosure relate to systems, apparatus, and methods of analyzing specimens.

BACKGROUND

In medical testing and processing, diagnostic analyzers (immunoassay instruments, clinical chemistry analyzers, in vitro analyzers, and the like) may be used to test for concentrations of one or more constituents (e.g., one or more analytes or other component(s)) contained within biological specimens, such as, blood or components thereof such as serum or plasma, urine, sputum, saliva, cerebrospinal liquids, and the like. Such diagnostic analyzers may be complex and may perform hundreds or even thousands of diagnostic tests on specimens each day.

If a fault occurs in a diagnostic analyzer, the diagnostic analyzer may have to be taken out of service until the fault is corrected. During this time, tests cannot be conducted and specimens may have to be sent to other analyzers or to other laboratories for testing, which is costly and time consuming.

SUMMARY

According to a first aspect, a method of analyzing a specimen is provided. The method of analyzing a specimen includes detecting a specimen integrity error in the specimen; capturing an image of the specimen; sending the image of the specimen to a customer support center at a remote location; analyzing the image of the specimen at the customer support center; and determining a cause of the specimen integrity error in response to analyzing the image of the specimen.

According to a second aspect, a diagnostic analyzer is provided. The diagnostic analyzer includes an imaging device configured to capture an image of a specimen; a detector configured to detect a specimen integrity error in the specimen; and a communication interface configured to transmit an image of the specimen to a customer support center at a remote location in response to the detector detecting a specimen integrity error.

According to a third aspect, a diagnostic system is provided. The diagnostic system includes a customer support center at a remote location; a diagnostic analyzer further including: an imaging device configured to capture an image of a specimen; an aspiration device configured to aspirate the specimen; a detector configured to carry out detection of a specimen integrity error comprising an artifact in the specimen; and a communication interface configured to transmit the image of the specimen to the customer support center in response to the detection of the artifact in the specimen, wherein the customer support center at the remote location is operational to prompt the diagnostic analyzer or an operator of the diagnostic analyzer to perform a corrective action in response to the detection of the specimen integrity error.

Still other aspects, features, and advantages of the disclosure may be readily apparent from the following detailed description illustrating a number of example embodiments. This disclosure may also be capable of different embodiments, and its several details may be modified in various respects. Accordingly, this disclosure covers all modifications, equivalents, and alternatives falling within the scope of claims.

DETAILED DESCRIPTION

A diagnostic analyzer may aspirate a liquid (e.g., a specimen) from a specimen container in order to perform one or more tests on the aspirated liquid. A specimen integrity error may occur when a fault is experienced by a diagnostic analyzer during aspiration and/or an artifact is present in a specimen. Faults occurring during aspiration may be the result of faulty pumps or leaky conduits that introduce air into the aspirated liquid, for example. The term "artifact" as used herein includes a clot, a bubble, or foam in a serum or plasma portion of the specimen. The term "clot" as used herein includes a coagulated mass present in the serum or plasma portion that is produced by clotting of whole blood. The term "bubble" as used herein includes an isolated substantially spherical pocket of gas in the serum or plasma portion that is not foam. Bubbles may have diameters between about 0.2 mm and about 1.0 mm, for example. The term "foam" as used herein includes a collection or grouping of small substantially spherical pockets of gas grouped together in close proximity to one another at a top of the serum or plasma portion. Individual ones of the spherical pockets of gas may have diameters of between about 0.1 mm to about 0.5 mm, for example.

Aspirating specimens containing bubbles or foam may result in aspiration of air, which may yield invalid test results. The presence of a clot may cause clogging of a pipette used to aspirate the specimen, which may cause disruption of the testing process or erroneous results. In addition, artifacts may affect the interpretation of results of pre-analytical testing, such as testing for an interferent such as hemolysis, icterus, and/or lipemia.

Specimen integrity errors, such as the presence of an artifact in a specimen, may be the result of malfunctions in the diagnostic analyzer, operator errors, and/or specimen processing errors. In conventional methods and diagnostic analyzers, an operator may call a service technician to make a visit to the laboratory upon detection of a specimen integrity error to determine the cause of the specimen integrity error and to correct the error. The service technician may be sent from the manufacturer of the diagnostic analyzer, which may be time consuming and costly. Moreover, the diagnostic analyzer may be out of use for an extended period while waiting for the service technician to arrive.

Figure 1:
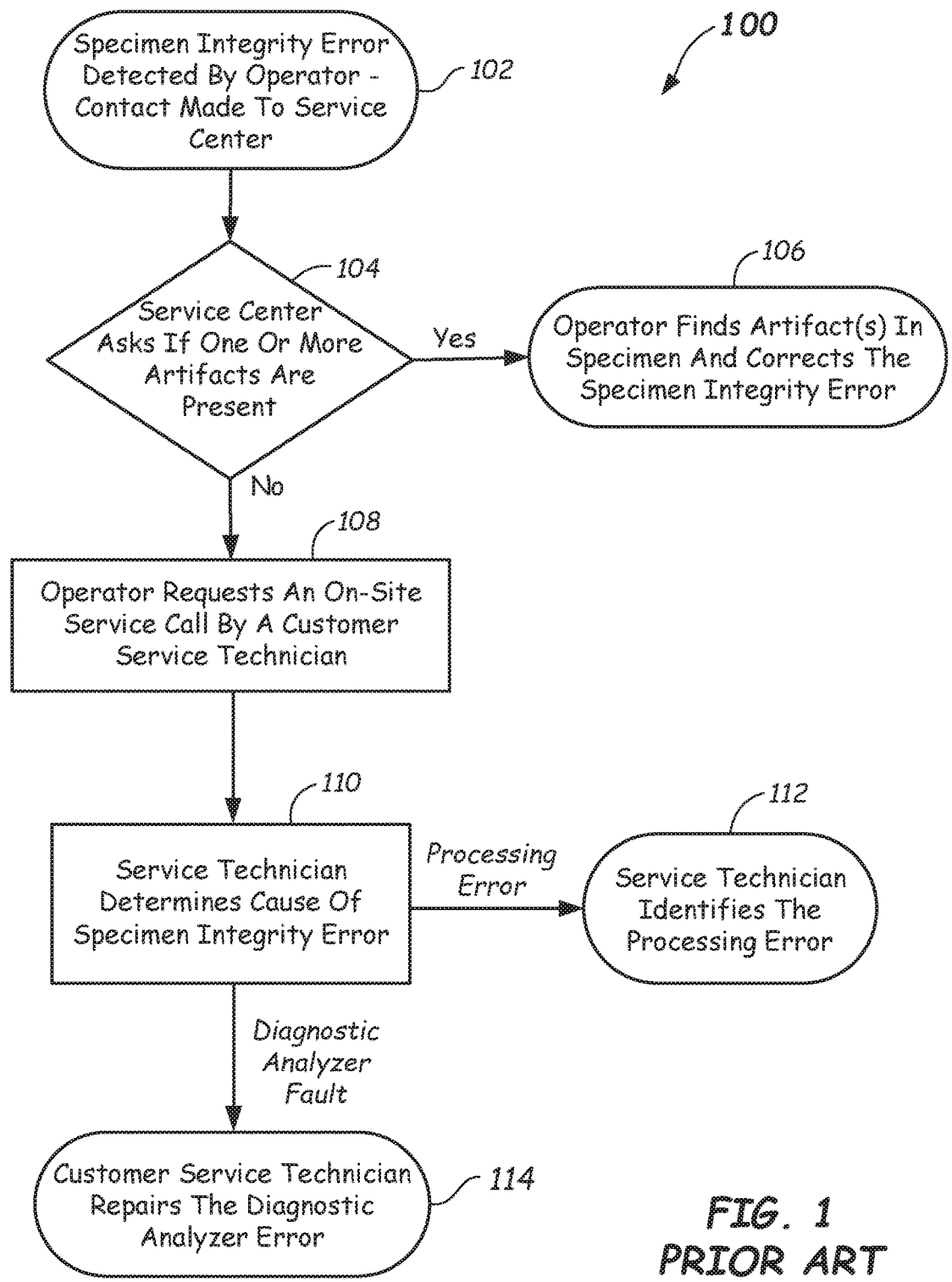
FIG. 1 illustrates a flowchart describing actions taken when a specimen integrity error is detected by an operator of a diagnostic analyzer according to the prior art.

FIG. 1 illustrates a flowchart describing a method 100 of manual actions taken when a specimen integrity error is detected by an operator of a conventional diagnostic analyzer. In block 102, a specimen integrity error is detected by the operator who then contacts a service center. In decision block 104, the service center asks the operator if one or more artifacts are present in the specimen. If the result of decision block 104 is affirmative, processing proceeds to block 106 where the operator finds the one or more artifacts and corrects the specimen integrity error. If the result of decision block 104 is negative, processing proceeds to block 108 where the operator requests an on-site service call from a service technician. Processing then proceeds to decision block 110 where the service technician determines the cause of the specimen integrity error. If there are one or more processing errors, processing proceeds to block 112 where the service technician identifies the one or more processing errors. The service technician may resolve the one or more processing errors that caused the specimen integrity error and specimen testing on the diagnostic analyzer may resume. If the result of decision block 110 is that the specimen integrity error is due to a fault in the diagnostic analyzer, processing proceeds to block 114 where the service technician repairs the diagnostic analyzer.

During the period that the service technician is in route to and on-site at the laboratory housing the diagnostic analyzer, testing may be stopped. During this period, specimens to be tested may be backed up or the specimens may have to be moved to other diagnostic analyzers or even shipped to other laboratories for testing.

In view of the foregoing, one or more embodiments of the disclosure provide methods, systems, and apparatus configured to remotely detect and/or remotely analyze specimen integrity errors and to notify the operator of a diagnostic analyzer of the errors and possible solutions to the errors. The remote detection and analyzing of the specimen integrity errors may be performed at a remote customer support center, for example. The diagnostic analyzer may be in communication with the remote customer support center. During analysis of a specimen, the customer support center may be notified if a specimen integrity error occurs. For example, during aspiration of a specimen, the diagnostic analyzer or the operator may communicate with the customer support center if an artifact is detected or an aspiration error occurs. Optionally, the customer support center may be notified if an artifact is detected during imaging of a specimen. The diagnostic analyzer then sends an image of the specimen to the customer support center. The diagnostic analyzer may also send data to the customer support center showing characteristics (e.g., operational data) of the diagnostic analyzer at the time that the specimen integrity error was detected. The customer support center may then determine a cause of the specimen integrity error. The customer support center may offer or prompt a solution to the error. In some embodiments, the customer support center may prompt the operator of the diagnostic analyzer to perform an action or prompt the diagnostic analyzer to automatically perform a procedure.

These and other aspects and features of embodiments of the disclosure are described herein with reference to FIGS. 2 through 6.

Figure 2:
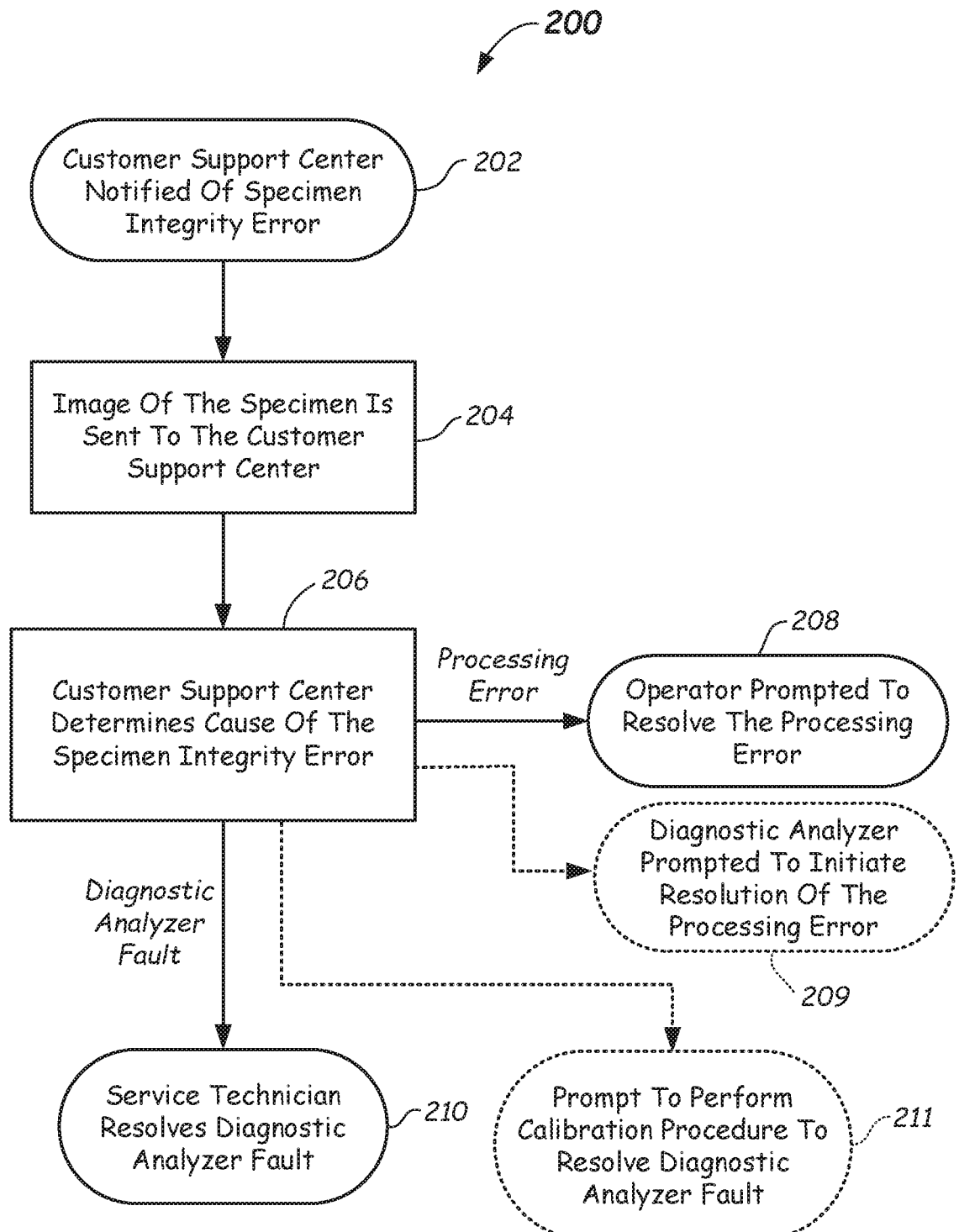
FIG. 2 illustrates a flowchart describing actions taken when a specimen integrity error is detected in a diagnostic analyzer according to one or more embodiments.

Reference is now made to FIG. 2, which illustrates a flowchart of an example of a method 200 of analyzing a specimen. According to certain aspects, the method 200 operates to remotely analyze and/or correct one or more specimen integrity errors. In block 202, a remote customer support center is notified of a specimen integrity error occurring in at least one specimen. The notification may be prompted by the operator or the notification may be automated by the diagnostic analyzer automatically notifying the customer support center of the specimen integrity error. In block 204, an image of the specimen (e.g., digital image) with or associated with the specimen integrity error is sent to the customer support center. Processing proceeds to decision block 206 where the cause of the specimen integrity error is determined at the customer support center.

In some embodiments, the customer support center may include a computer that provides an automated solution to the operator. For example, the image of the specimen may be analyzed with a trained model (e.g., a trained neural network such as a convolutional neural network) that determines the cause of the specimen integrity error. If the outcome of decision block 206 is that a processing error caused the specimen integrity error, the operator may be instructed to resolve the processing error as described in block 208. For example, in some embodiments, the operator may be notified of the processing error and prompted with one or more instructions to make one or more changes related to processing to fix the processing error. For example, the operator may be instructed to re-centrifuge the specimen or aspirate out foam from the specimen. In some embodiments, the operator may be instructed to realign and/or recalibrate a pipette used to aspirate the specimen. Such realignment and/or recalibration may properly align the pipette with the specimen during aspiration.

In some embodiments, the customer support center may prompt or instruct the diagnostic analyzer to resolve the processing error with or without input from the operator. In some embodiments, one or more instructions for resolving the processing error may be sent electronically from the customer support center to the diagnostic analyzer. In some embodiments, the instructions may instruct the diagnostic analyzer to perform one or more automated calibration or alignment procedures to resolve the processing error. The one or more automated calibration or alignment procedures may include realigning and/or recalibrating a pipette used to aspirate the specimen. In some embodiments, the customer support center may instruct the diagnostic analyzer to send the specimen to a centrifuge station or a station that aspirates foam from the specimen.

If the outcome of decision block 206 is that the specimen integrity error is the result of a fault in the diagnostic analyzer, processing proceeds to block 210 where a service technician resolves the fault in the diagnostic analyzer. For example, a service technician may be sent to the laboratory to resolve the fault in the diagnostic analyzer. Some examples of a fault may include a valve or a pump that is inoperable, a leak in a pressure/fluid line, an obstruction in a line, or an improperly positioned pipette. Resolving the fault may include repairing and/or recalibrating other components of the diagnostic analyzer.

Figure 3:
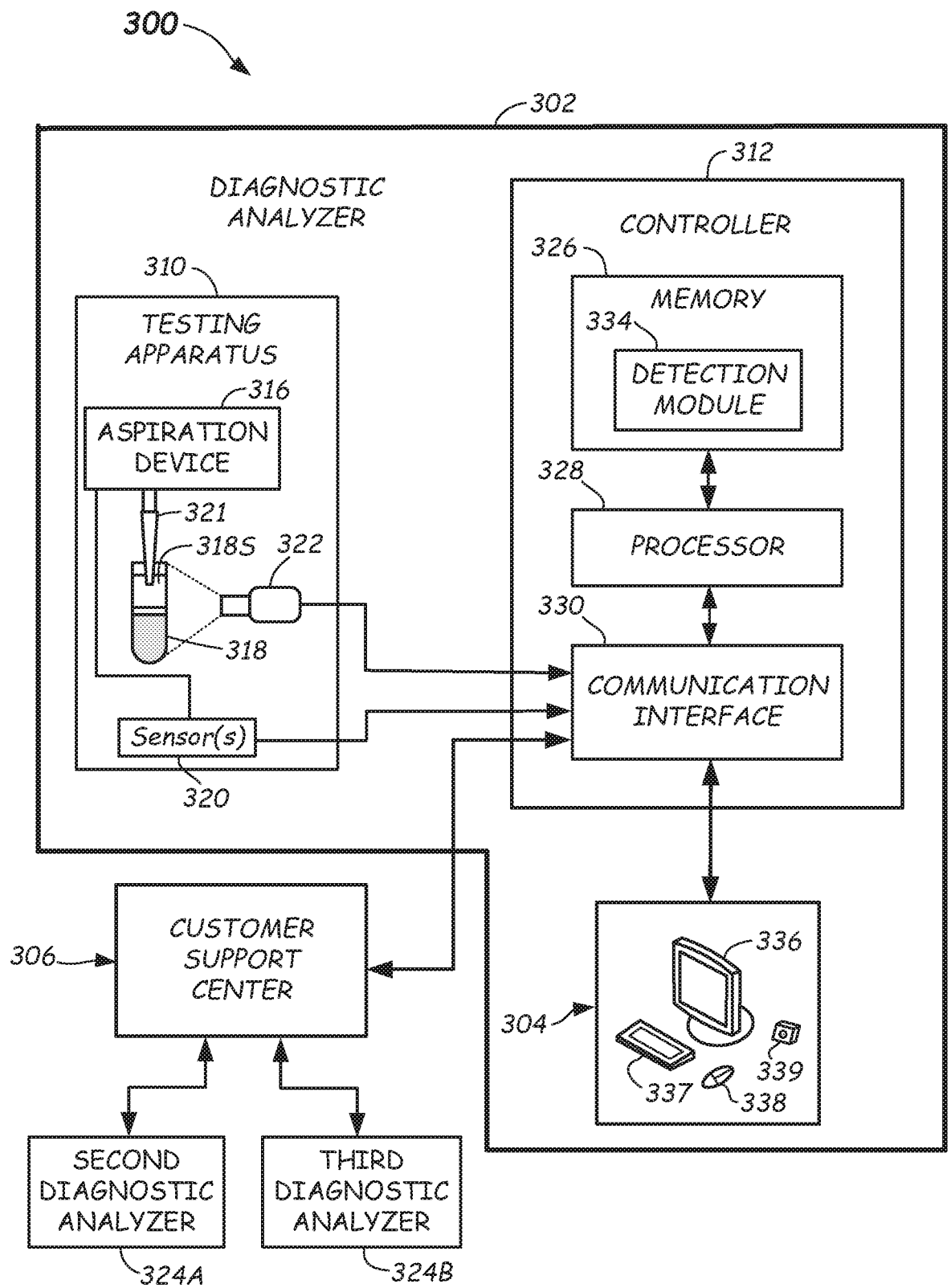
FIG. 3 illustrates a schematic block diagram of a diagnostic system according to one or more embodiments.

Reference is now made to FIG. 3, which illustrates a schematic block diagram of a diagnostic system 300. The diagnostic system 300 may include a diagnostic analyzer 302 including a user interface 304, and a customer support center 306. The diagnostic analyzer 302 may be in electronic communication with the customer support center 306. In some embodiments, the user interface 304 may include a monitor 336, a keyboard 337, and/or a mouse 338 and is useful for providing data input and manipulation relative to the operation of the diagnostic analyzer 302. The customer support center 306 may be remote from the diagnostic analyzer 302 and/or any laboratory or building that houses the diagnostic analyzer 302. The customer support center 306 may be in communication with multiple customers (e.g., diagnostic analyzers).

The diagnostic analyzer 302 may be configured to perform one or more diagnostic tests and/or analysis on biological specimens. For example, the diagnostic tests and/or analysis on biological specimens may include, but are not limited to, testing for a concentration of an analyte, protein, or nucleic acid or other constituent in a specimen. The diagnostic analyzer 302 may include a testing apparatus 310 and a controller 312 electronically coupled thereto. The testing apparatus 310 may include an aspirating device 316 that may be configured to aspirate a liquid (e.g., specimen 318S) from a specimen container 318 (e.g., specimen collection test tube). One or more sensors 320 may monitor the aspiration. An imaging device 322 may capture one or more images of a specimen container 318 and the specimen (e.g., including liquid) located therein. Imaging device 322 may be included in the testing apparatus 310 or may be outside of the testing apparatus 310, such as in a quality check apparatus, which may be located on a track delivering the specimen container 318 to the testing apparatus 310. Other diagnostic analyzers, such as a second diagnostic analyzer 324A and a third diagnostic analyzer 324B also may be electronically communicating with the customer support center 306. The second diagnostic analyzer 324A and the third diagnostic analyzer 324B may be identical or substantially similar to the diagnostic analyzer 302.

The controller 312, which may be a computer device, may include a memory 326 (e.g., RAM, ROM, or other memory type) configured to store programming instructions, test result data, digital images captured by the imaging device 322, and/or other information/data. The controller 312 may also include a processor 328 (e.g., a CPU, microprocessor, or the like) configured to execute programming instructions in connection with the operation of the diagnostic analyzer 302. The controller 312 may further include a communication interface 330, which the controller 312 may use to electronically communicate with the diagnostic analyzer 302, the user interface 304, the one or more sensors 320, and the customer support center 306. In some embodiments, the communication interface 330 may enable communication with a network (not shown) coupled between the controller 312 and the customer support center 306. The network may include a local area network (LAN), a wireless local area network (WLAN), a power line communication (PLC) network, the internet, other wireless protocol, or the like.

The communication interface 330 may be configured to receive analyzer results from the testing apparatus 310 in response to the testing apparatus 310 processing the specimen container 318 or the specimen 318S located therein. The communication interface 330 may also be configured to receive data (e.g., pressure data or pressure traces) related to the testing apparatus 310 obtained during aspiration, for example. In some embodiments, the one or more sensors 320 may measure pressure and/or collect pressure data from the aspiration device 316 during an aspiration process and send the pressure data to the communication interface 330. The communication interface 330 may also receive image data generated by the imaging device 322 when the imaging device 322 captures an image of the specimen container 318 and/or the specimen 318S located therein.

Data related to the testing apparatus 310 and/or operations thereof may be provided by the one or more sensors 320 (e.g., pressures sensor(s), temperature sensor(s), bar code reader(s), barometer(s), etc.). The one or more sensors 320 may be internal and/or external to the testing apparatus 310 and may be configured to provide various readings or measurements of at least some of the data related to the operation of the testing apparatus 310. This related data may include, but is not limited to, one or more of the following: aspiration pressure reading, process step, number and/or type of test performed, internal temperature of the testing apparatus 310, humidity level, and/or atmospheric pressure. Other types of data related to the operation of the testing apparatus 310 may additionally or alternatively be included.

The controller 312 may also include a detector embodied in software as a detection module 334, stored in memory 326, and executable by the processor 328. The detection module 334 may include instructions that are executable on the processor 328. The detection module 334 may be configured and operable to compare test results from the testing apparatus 310 with expected results from a quality control test or other data. The detection module 334 may also be configured to analyze data from the one or more sensors 320 and/or the imaging device 322 in order to detect a specimen integrity error, such as an artifact present in the specimen 318S.

In some embodiments, the detection module 334 may include an artificial intelligence-driven trained model that identifies patterns in the data related to the testing apparatus 310 and/or images of the specimen 318S that may indicate a specimen integrity error.

The detection module 334 may cause the communication interface 330 to notify the customer support center 306 in response to detection of a specimen integrity error as described in block 202 (FIG. 2) of the method 200. The notification may be manual or automated. The communication interface 330 may send image data representative of an image of the specimen 318S with the specimen integrity error as a notification to the customer support center 306 as described in block 204 (FIG. 2) of the method 200. The notification may be received over the communication network as data, wherein the receipt of the data initiates a review by the customer support center 306. In some embodiments, the image of the specimen 318S may be displayed on a monitor 336 of the user interface 304. In some embodiments, the communication interface 330 may also send data from the one or more sensors 320 related to the specimen integrity error to the customer support center 306 and/or the user interface 304 where the data may be displayed on the monitor 336.

In some embodiments, during processing of the specimen 318S, the controller 312 may send a signal via the communication interface 330 to the user interface 304 indicating that a specimen integrity error has occurred. For example, the controller 312 may cause an alarm 339 to notify the operator of the specimen integrity error. In other embodiments, a signal or notification may be displayed on the monitor 336. The controller 312 may also send an image of the specimen 318S and/or the data from the one or more sensors 320 to the user interface 304. In some embodiments, the operator may manually notify the customer support center 306 that a specimen integrity error has occurred. For example, the operator may send the image of the specimen 318S and/or the data to the customer support center 306. In some embodiments, the operator may send a signal from the user interface 304 to the communication interface 330 that causes the communication interface 330 to send the image of the specimen 318S and/or the data to the customer support center 306.

In some embodiments, the controller 312 may automatically send the notice of a specimen integrity error to the customer support center 306. For example, if the detection module 334 detects a specimen integrity error, the detection module 334 may cause the controller 312 to send the notice to the customer support center 306. The notice may include image data representative of the specimen having the specimen integrity error and possibly also the data from the one or more sensors 320.

When the customer support center 306 receives notice of the specimen integrity error, the customer support center 306 may determine the cause of the specimen integrity error as described in decision block 206 (FIG. 2) of the method 200. For example, personnel or a computer in the customer support center 306 may analyze the image of the specimen 318S to determine if an artifact is present in the specimen 318S. Embodiments or devices and methods or analyzing a specimen to determine if artifacts are present are described in U.S. Patent Application 2019/0033230, which is herein incorporated by reference in its entirety for all purposes. Personnel in the customer support center 306 or a computer located therein may also analyze data from the one or more sensors 320 and/or other data to determine the cause of the specimen integrity error.

For example, if a certain number of consecutive specimens being aspirated by the aspiration device 316 have pressure anomalies indicative of artifacts noted by the one or more sensors 320, such as detecting a low pressure during aspiration, the customer support center 306 may determine that a fault exists in the diagnostic analyzer 302. As described in block 210 (FIG. 2) of the method 200, the customer support center 306 may dispatch a service technician to the diagnostic analyzer 302 to resolve the diagnostic analyzer fault. In some embodiments, the customer support center 306 may optionally, in block 211, prompt the operator to perform a calibration procedure, such as an auto-calibration of the positioning of the pipette 321 of the aspiration device 316 to resolve the fault in the diagnostic analyzer 302. Optionally, the prompt may be directly to the diagnostic analyzer to perform an automatic calibration procedure, such as an auto-calibration of the positioning of the pipette 321.

If the specimen integrity error occurs occasionally, the customer support center 306 may determine that an error exists with processing of the specimen 316S. As described in block 208 (FIG. 2) of the method 200, the customer support center 306 may prompt the operator with one or more suggestions for the operator to try to fix the processing error. For example, if aspiration pressure is low, an artifact of a bubble or foam may be present in the specimen 316S. The customer support center 306 may prompt the operator to check centrifuging processes applied to the specimen or prompt removal of the artifact of a bubble or foam.

In some embodiments, the customer support center 306 may prompt the diagnostic analyzer 302 with one or more instructions to resolve the processing error. For example, the customer support center 306 may instruct the diagnostic analyzer 302 to initiate resolution of the processing error in block 209, such as by implementing one or more corrective processes, such as a re-centrifugation of the specimen or clot removal, which may be performed automatically and without input from the operator.

Figure 4A:
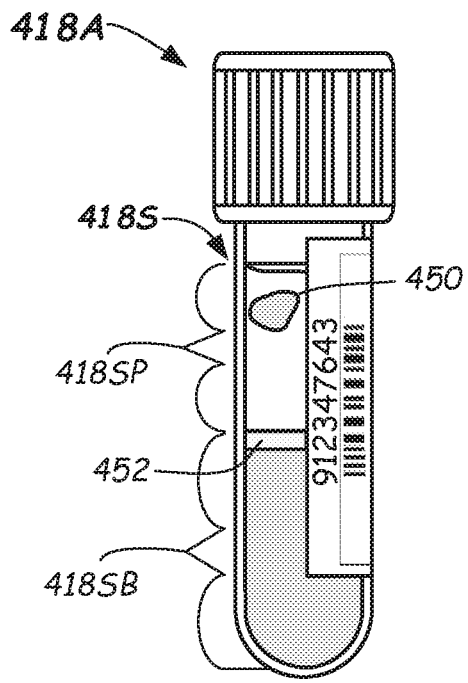
FIG. 4A illustrates a specimen container including a specimen with a clot artifact located therein according to one or more embodiments.
Figure 4B:
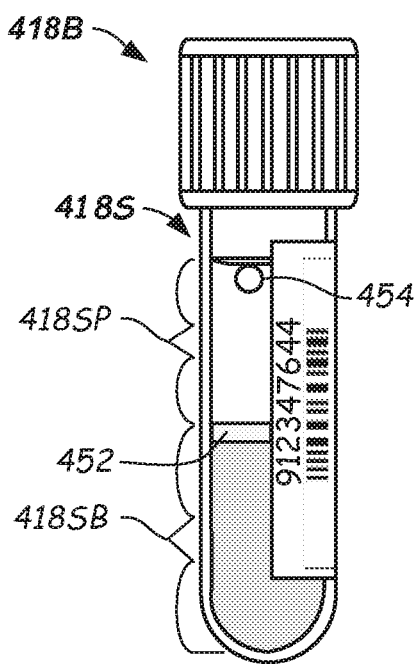
FIG. 4B illustrates a specimen container including a specimen with a bubble artifact located therein according to one or more embodiments.
Figure 4C:
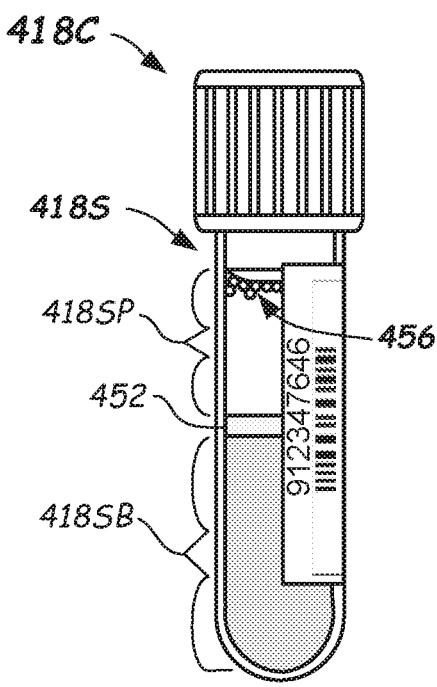
FIG. 4C illustrates a specimen container including a specimen with a foam artifact located therein according to one or more embodiments.

Reference is now made to FIGS. 4A-4C where specimen containers (418A-418C), such as the specimen container 318 (FIG. 3), including various artifacts, are shown. The artifacts described herein are selected from a group including a clot, a bubble, and foam. FIG. 4A illustrates a specimen container 418A including a specimen 418S and an artifact that is a clot 450 located therein. The specimen 418S may be separated into a serum or plasma portion 418SP and a settled blood portion 418SB, such as by centrifuging the specimen container 418A. A gel separator 452 may optionally separate the serum or plasma portion 418SP from the settled blood portion 418SB. The clot 450 may be a thick, viscous, or coagulated mass or lump, such as blood that is not in the settled blood portion 418SB. The clot 450 may be free-floating within the serum or plasma portion 418SP. The clot 450 may prevent the specimen 318S from being aspirated by the aspirating device 316 (FIG. 3) and may be detected by a high-pressure value experienced in the pressure trace as determined by the one or more sensors 320 (FIG. 3) during aspiration. For example, the clot 450 may block the aspiration device 316 and prevent aspiration of the serum or plasma portion 418SP. If the clot 450 is detected such as by a pressure anomaly, analysis of the captured image of the specimen container 418A may be performed remotely at the customer support center 306 (FIG. 3) as described herein to verify the presence of a clot.

FIG. 4B illustrates a specimen container 418B including a specimen 418S and an artifact that is a bubble 454 located therein. The bubble 454 may be a substantially circular pocket of gas contained in the serum or plasma portion 418SP. In some embodiments, one or more artifacts comprising a bubble may be contained in the serum or plasma portion 418SP. The bubble 454 may be adhered to a wall of the specimen container 418B or arranged at a top surface of the serum or plasma portion 418SP, for example. The bubble 454 may cause aspiration errors during aspiration. During the aspiration process, the bubble 454 may cause the one or more sensors 320 (FIG. 3) to measure a relatively lower pressure than expected. If a low-pressure measurement occurs, analysis of the specimen container 418B may be performed remotely at the customer support center 306 (FIG. 3) as described herein to determine if an artifact comprising a bubble is present.

FIG. 4C illustrates a specimen container 418C including a specimen 418S with the presence of foam 456. The foam 456 may be a collection or grouping of substantially circular pockets of gas contained in the serum or plasma portion 418SP located along the top surface of the serum or plasma portion 418SP, for example. The foam 456 may cause errors during aspiration. During the aspiration process, the foam 456 may cause the one or more sensors 320 (FIG. 3) to measure a relatively lower pressure than expected. If a low-pressure measurement occurs, analysis of the specimen container 418C may be performed remotely at the customer support center 306 (FIG. 3) as described herein to determine if a foam artifact is present.

The presence of one or more artifacts in the serum or plasma portion 418SP may affect the interpretation of results of pre-analytical testing, such as testing for an interferent such as hemolysis, icterus, and/or lipemia, but also of the subsequent analytical testing. The presence of a clot may cause clogging of the pipette 321 (FIG. 3) used for aspiration of the serum or plasma portion 418SP, which may cause disruption of the testing process.

Figure 5:
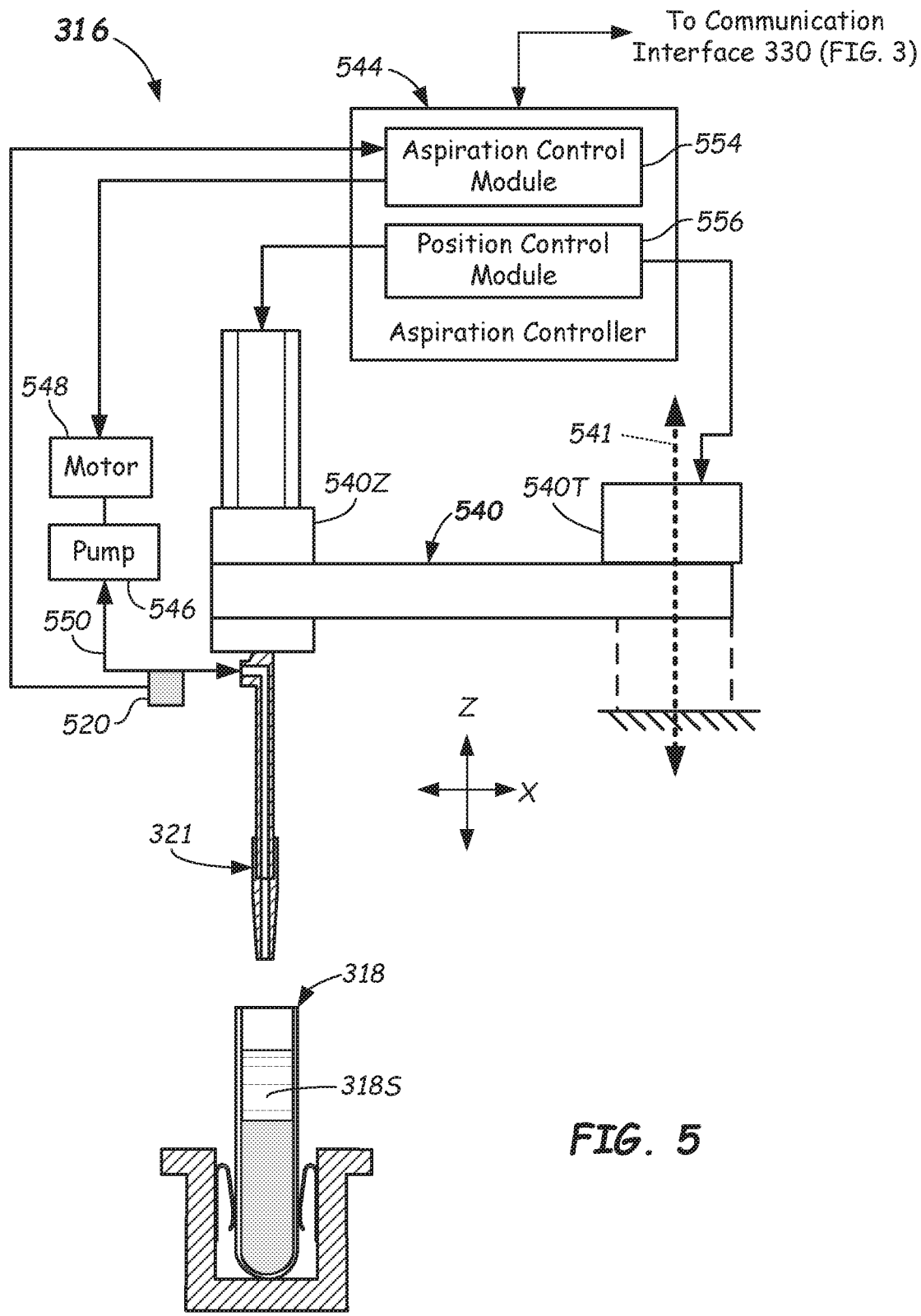
FIG. 5 illustrates a partially cross-sectioned side view of an aspiration device of a diagnostic analyzer according to one or more embodiments.

Reference is now made to FIG. 5, which illustrates a partial cross-sectioned view of an embodiment of the aspiration device 316. The aspiration device 316 may be used to precisely transfer a desired volume of the specimen 318S from one location to another. For example, the aspiration device 316 may be used to aspirate a precise volume of the specimen 318S from the specimen container 318 and then dispense the specimen 318S at another location or into another vessel, such as to a cuvette or well plate. The aspiration device 316 may be used to transfer a precise volume of the specimen 318S.

The aspiration device 316 may include a robot 540 having the pipette 321 coupled thereto. The pipette 321 may be either directly connected to or interconnected to a robotic component 540Z of the robot. The pipette 321 may be moveable in space by the robot 540. The aspiration device 316 may include an aspiration controller 544 that may command the robot 540 and attached pipette 321 to move in coordinate space. For example, the robot 540 may move the pipette 321 to one or more defined locations in space as commanded by the aspiration controller 544. In particular, the aspiration controller 544 may command the robot 540 to move in one or more coordinate directions (e.g., in an X, Y, or Z direction), two or more coordinate directions (e.g., X and Z, Y and Z, or theta and Z), three or more coordinate directions (e.g., X, Y, and Z, or theta, R, and Z), where X is side-to-side motion, Y is motion into and out of the paper in FIG. 5, theta is rotational motion about an axis (e.g., axis 541), R is extension and retraction motion perpendicular to the axis 541, and Z is vertical motion. The aspiration controller 544 may be a suitable electronic controller configured to interact with the robot 540 and may include a suitable microprocessor, memory, power supply, conditioning electronics, one or more feedback sensors, and electronic circuitry adapted to carry out the one or more coordinate motions of the pipette 321.

In some embodiments, the aspiration controller 544 may be incorporated into the controller 312 (FIG. 3) described above. Accordingly, the components of the aspiration controller 544 may be included within the controller 312. In some embodiments, the aspiration controller 544 is separate from the controller 312, but they are in electronic communication via the communication interface 330 (FIG. 3).

The robotic component 540Z may accomplish a vertical motion of the pipette 321 in the Z direction. Theta motor 540T can then cause motion in the theta direction (about axis 541) to a location above the specimen container 318 wherein the specimen 318S located in the specimen container 318 may be aspirated. Aspiration may involve lowering the pipette 321 in the Z direction to a point in the specimen container 318 where the specimen 318S is located. A portion of the specimen 318S may then be aspirated into the pipette 321.

The aspiration device 316 may include a pump 546 that may be connected to the pipette 321 via conduit 550 and driven to aspirate and/or dispense accurate volumes of liquid, such as the specimen 318S. The pump 546 may be driven by a pump motor 548, such as a stepper motor, for example. Other suitable motors may be used. The pump 546 may be any type of pump suitable for dispensing relatively precise liquid volumes, such as a piston pump. A conduit 550 may be coupled between the pump 546 and the pipette 321.

The pump 546 may be driven in response to control signals from an aspiration control module 554 of the aspiration controller 544. The aspiration control module 554 may be a separate part of the aspiration controller 544 or integrated with a position control module 556. For example, the aspiration control module 554 and the position control module 556 each may include suitable control signal conditioning components such as filters, analog-to-digital converters, and/or amplifiers to send signals to the pump motor 548 and robot 540 and receive feedback signals therefrom. The aspiration controller 544 may include a microprocessor and memory for carrying out pre-programmed position and aspiration control instructions. In some embodiments, separate intercommunicating microprocessors and memories may be used to carry out position control and aspiration control.

The aspiration device 316 may include a pressure sensor 520 fluidly coupled to the pipette 321. The pressure sensor 520 may be configured to sense representative aspiration pressure associated with the pipette 321 and generate one or more electronic signals (e.g., voltage signals) representative of the aspiration pressure, such as a pressure signal trace. The aspiration control module 554 may receive the one or more electronic signals from the pressure sensor 520 and use the one or more signals during the aspiration process. The pressure sensor 520 may be configured to measure and output pressure values and/or data associated with the aspiration by the pipette 321. For example, the pressure sensor 520 may be coupled to the pipette 321 or, as shown, coupled to the conduit 550 fluidly connecting the pump 546 and the pipette 321. Accordingly, the pressure sensor 520 may measure aspiration pressure in the pipette 321.

During the aspiration process, the robot 540 may position the pipette 321 above the specimen container 318 and descend the pipette 321 into the specimen container 318. The descent into the specimen container 318 is produced by the robotic component 540Z under the control of the position control module 556 until the pipette 321 reaches a desired depth therein. At this time, the aspiration device 316 may be operated via signals from the aspiration control module 554 to draw off a predefined volume of the specimen 318S into the interior of the pipette 321.

In some embodiments, the aspirated volume can be less than about 25 µL, but aspirations larger than about 25 µL could also be performed. As the pump 546 is operated, the level of specimen 318S in the specimen container 318 is attempted to be drawn down (aspirated). When it is determined that a desired volume of specimen 318S has been received within the pipette 321, as measured by the aspiration control module 554, the pump 546 may be stopped such that no further aspiration of the specimen 318S occurs. This may be determined by a suitable feedback sensor (not shown) on the pump motor 548 providing feedback on the position of the pump 546 or counting steps of the pump motor 548 when the pump motor 548 is a stepper motor, for example. Other suitable position feedback may be provided.

During the aspiration process, a representative raw aspiration pressure may be measured (e.g., the measured aspiration pressure or trace) by the pressure sensor 520. This raw measured pressure or pressure trace may be conditioned by sensor conditioning devices (not shown) to provide a pressure signal to the aspiration control module 554. Other pressure sensors located at other locations in the aspiration device 316 may be provided to measure pressure during the aspiration process.

Aspiration processes, aspiration devices, and methods of detecting specimen integrity errors and specimen artifacts are described in U.S. Pat. No. 9,915,674, which is herein incorporated by reference it its entirety for all purposes. In some embodiments, sample integrity may be determined by analyzing the pressure signal. In some embodiments, the pressure signal may be analyzed by the controller 312 (FIG. 3). For example, the pressure signal may be compared to one or more predetermined pressure values to determine whether the pressure signal is above, below, or within a predetermined limit(s).

In some embodiments, if the pressure signal is greater than (e.g., has a higher absolute value) than a first predetermined pressure limit value and lower than a second predetermine pressure limit value, then the aspiration may be deemed to be successful and no specimen integrity errors may be detected. If the pressure signal has an absolute value that is above the second predetermined pressure limit value, then the aspiration may be deemed to be unsuccessful or incomplete and a sample integrity error may be noted. This sample integrity error may signify that a clot was aspirated. If the pressure signal has an absolute value that is below the first predetermined pressure limit value, then the aspiration may be deemed to be unsuccessful or incomplete and a sample integrity error may be noted. This sample integrity error may signify that some air was aspirated, such as due to a leak between the pump 546 and the pipette 321 (FIG. 3) or other aspiration apparatus malfunction and/or a bubble or foam in the specimen 318S (FIG. 3). The controller 312 (FIG. 3) may then take an action as described herein, such as sending an image of the specimen 318S and/or the pressure signal to the customer support center 306 (FIG. 3).

In some embodiments, the pressure signal may be compared to a predetermined pressure value and a specimen integrity error may be determined in response to the pressure signal exceeding the predetermined pressure value. For example, if the pressure signal exceeds the predetermined pressure value, the controller 312 may determine that an artifact comprising a clot is present in the specimen 318S and may take actions described herein. In some embodiments, the controller 312 (FIG. 3) may then take actions as described herein, such as sending an image of the specimen 318S and/or the pressure signal to the customer support center 306.

In some embodiments, the pressure signal may be compared to a first predetermined upper pressure value limit and a second predetermined lower pressure value limit. A specimen integrity error may be determined in response to the pressure signal exceeding the first upper predetermined pressure value or being less than the second predetermined lower pressure value. For example, if the pressure signal exceeds the first predetermined upper pressure value limit, the controller 312 may determine that a clot artifact is present in the specimen 318S. If the pressure signal is less than the second predetermined lower pressure value limit, the controller 312 may determine that at least some air was aspirated. The air may be the result of an artifact comprising a bubble or foam in the specimen 318S and/or a leak between the pump 546 and the pipette 321. The controller 312 (FIG. 3) may then take actions as described herein, such as sending an image of the specimen 318S and/or the pressure signal to the customer support center 306 for further analysis.

In other embodiments, artifacts may be detected by visual analysis using optical machine learning. Such embodiments are described in U.S. Patent Application 2019/0033230, which is incorporated by reference herein in its entirety for all purposes. For example, an image of the specimen 318S may be captured and sent to the controller 312. The controller 312 may include a trained model (such as a neural network or other model-based network) and may use artificial intelligence to analyze the image of the specimen 318S to determine if an artifact is present. Upon detection of an artifact, the controller 312 may send the image of the specimen 318S and/or aspiration pressure data to the customer support center 306 as described herein.

In some embodiments, the image of the specimen 318S may be captured at locations other than the testing apparatus 310. For example, the imaging device 322 may be located within other devices or apparatus within the diagnostic analyzer 302. In some embodiments, the diagnostic analyzer 302 may have a quality check module where the specimen 318S is analyzed prior to aspiration. In such embodiments, the image of the specimen may be captured in the quality check module. In some embodiments, the specimen 318S may be aspirated at locations other than the testing apparatus 310. In these embodiments, aspiration pressure may be measured as described herein and used to identify a sample integrity error.

The customer support center 306 (FIG. 3) may have personnel and/or one or more computers trained to identify and offer solutions to correct one or more sample integrity errors. These personnel may have more experience in diagnosing and correcting sample integrity errors than operators of the diagnostic analyzer 302. The one or more computers may have trained models and/or software that are more powerful than software in the controller 312 to identify and offer solutions to correct one or more sample integrity errors. Accordingly, the customer support center 306 may determine that a sample integrity error has occurred and may prompt the operator to alleviate the sample integrity error faster than the operator acting alone. In some embodiments, diagnostic analyzers from a plurality of laboratories may be in communication with the customer support center 306. Accordingly, the customer support center 306 may service many laboratories including analyzers, which helps personnel in the customer support center 306 gain more experience diagnosing and correcting sample integrity errors.

Figure 6:
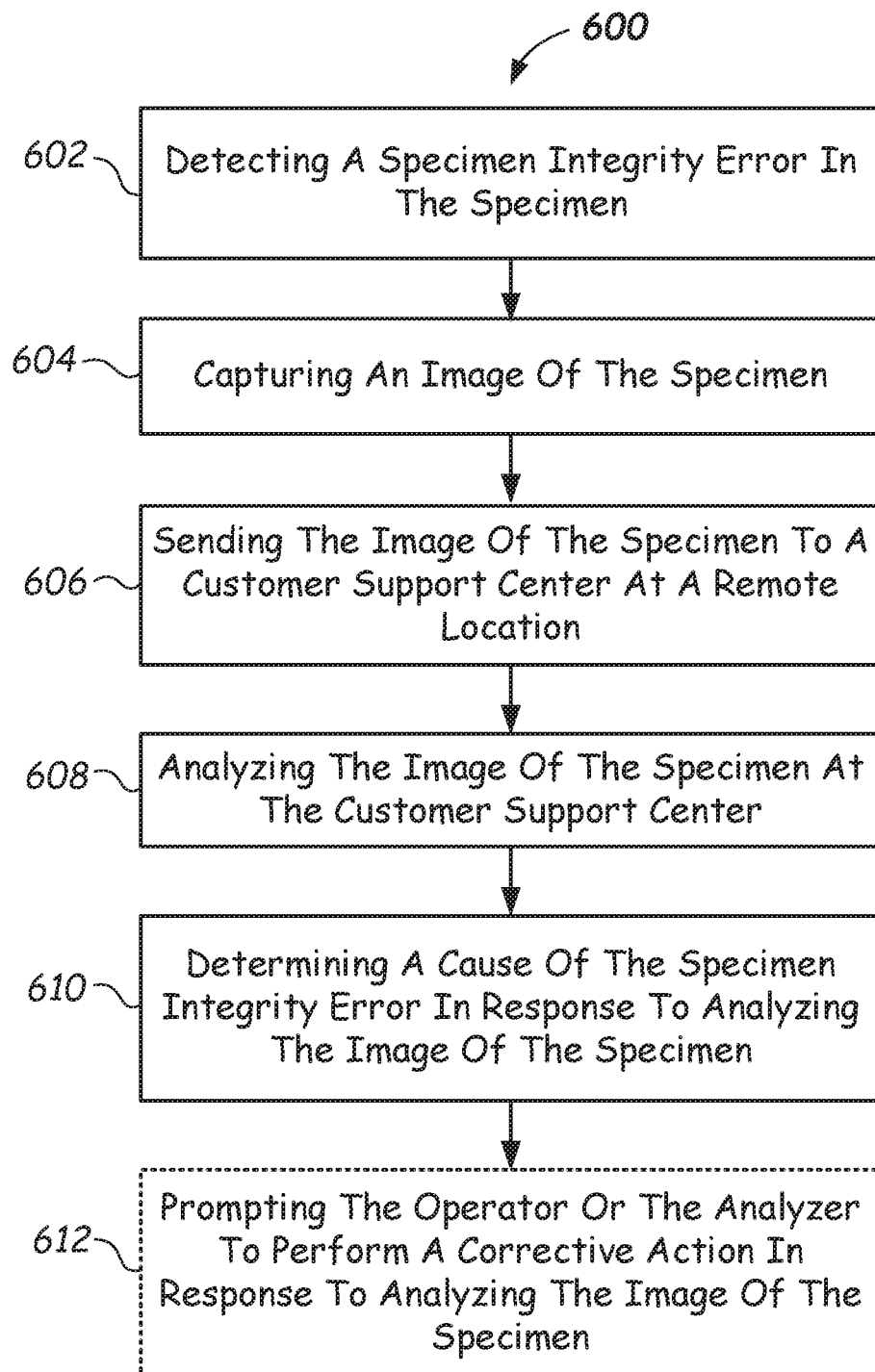
FIG. 6 illustrates a flowchart describing a method of analyzing a specimen according to one or more embodiments.

Reference is now made to FIG. 6 which illustrates a flowchart of a method 600 of analyzing a specimen (e.g., specimen 318S). The method 600 includes, in 602, detecting a specimen integrity error in the specimen. The method 600 includes, in 604, capturing an image of the specimen. The method 600 includes in, 606, sending the image of the specimen to a customer support center (e.g., customer support center 306) at a remote location (e.g., in another facility). The method 600 includes, in 608, analyzing the image of the specimen at the customer support center. The method 600 includes, in 610, determining a cause of the specimen integrity error in response to analyzing the image of the specimen.

The method 600 can further optionally includes, in 612, prompting the operator or a diagnostic analyzer (e.g., diagnostic analyzer 302) to perform a corrective action in response to analyzing the image of the specimen.

While specific apparatus and methods have been shown by way of example embodiments herein, it should be understood that other and different embodiments are possible. This disclosure is intended to cover all modifications, equivalents, and alternatives falling within the scope of the following claims.

What is claimed is:

1. A method of analyzing a specimen, comprising:
  processing the specimen using a diagnostic analyzer;
  detecting a specimen integrity error in the specimen via a detection module executed by a processor of the diagnostic analyzer, the detection module configured to receive sensor values from sensors of the diagnostic analyzer and to identify sensor value anomalies indicative of specimen integrity errors;

capturing an image of the specimen via an imaging device;

sending, via the detection module, the image of the specimen to a customer support center at a remote location;

analyzing the image of the specimen at the customer support center via one or more computers of the customer support center configured via a trained model to identify artifacts in the image of the specimen; and determining, via the customer support center, a cause of the specimen integrity error to be one or more errors in the diagnostic analyzer in response to analyzing the image of the specimen.

2. The method of claim 1, further comprising determining the cause of the specimen integrity error to be one or more specimen processing errors in response to analyzing the image of the specimen.

3. The method of claim 1, wherein the processing of the specimen comprises attempting to aspirate the specimen.

4. The method of claim 3, further comprising sending data of one or more pressure values acquired during the attempt to aspirate the specimen to the customer support center.

5. The method of claim 4, wherein the detecting the specimen integrity error via the detection module executed by the processor comprises analyzing data of the one or more pressure values acquired during the attempt to aspirate to determine whether any of the one or more pressure values exceeds a first threshold value or falls below a second threshold value.

6. The method of claim 1, wherein the analyzing of the image of the specimen comprises identifying a presence of an artifact comprising a clot in the image of the specimen.

7. The method of claim 1, wherein the analyzing the image of the specimen comprises identifying a presence of an artifact comprising a bubble in the image of the specimen.

8. The method of claim 1, wherein the analyzing the image of the specimen comprises identifying a presence of an artifact comprising foam in the image of the specimen.

9. The method of claim 1, further comprising prompting a solution to the specimen integrity error from the customer support center.

10. The method of claim 9, wherein the prompting of the solution comprises prompting an automated solution to the specimen integrity error to be carried out by the diagnostic analyzer.

11. The method of claim 10, wherein the automated solution to the specimen integrity error comprises one or more instructions to change processing of the specimen.

12. The method of claim 10, wherein the automated solution to the specimen integrity error comprises one or more instructions to perform one or more changes to the diagnostic analyzer.

13. The method of claim 1, wherein the detecting a specimen integrity error further comprises analyzing an image of the specimen using a trained model executed by a controller of the diagnostic analyzer to detect an artifact in the specimen.

14. The method of claim 13, wherein the artifact comprises a clog, a bubble, or foam.

15. A diagnostic analyzer, comprising:

an imaging device configured to capture an image of a specimen;

an aspiration device configured to aspirate the specimen;

a detector configured to detect a specimen integrity error in the specimen, wherein the detector comprises a pressure sensor configured to measure pressure in the aspiration device during at least a portion of an aspiration, and wherein the detector detects a specimen integrity error in response to a pressure measurement exceeding a first threshold value or falling below a second threshold value;

a communication interface configured to transmit an image of the specimen to a customer support center at a remote location in response to the detector detecting a specimen integrity error; and a controller configured to receive via the communication interface a corrective action from the customer support center to perform an automated calibration or alignment procedure in the aspiration device, or a re-centrifugation of the specimen, or a removal of a clot, foam, or bubble from the specimen.

16. The diagnostic analyzer of claim 15, wherein the communication interface is configured to transmit pressure measured during the aspiration to the customer support center.

17. The diagnostic analyzer of claim 15, wherein the specimen integrity error comprises an artifact in the specimen and wherein the detector includes a model trained to identify the artifact in the specimen based on the image of the specimen.

18. The diagnostic analyzer of claim 15, wherein the detector includes an artificial intelligence-driven trained model to identify patterns in sensor data or images of the specimen to identify a specimen integrity error.

19. A diagnostic system, comprising:

a customer support center at a remote location, the customer support center comprising one or more computers having a trained model configured to identify an artifact in an image of a specimen; and a diagnostic analyzer further comprising:

an imaging device configured to capture an image of a specimen;

an aspiration device configured to aspirate the specimen;

a detector configured to carry out detection of a specimen integrity error comprising an artifact in the specimen via one or more pressure measurement anomalies from one or more pressure sensors in the aspiration device; and a communication interface configured to transmit the image of the specimen to the customer support center in response to the detection of the artifact in the specimen, wherein the customer support center at the remote location is operational to prompt the diagnostic analyzer or an operator of the diagnostic analyzer to perform a corrective action in response to the detection of the specimen integrity error by the detector and identification of the artifact in the captured image of the specimen by the customer support center.

20. The diagnostic system of claim 19, wherein the customer support center identifies the artifact to be foam and the corrective action comprises instructing the diagnostic analyzer to send the specimen to a station that aspirates foam from the specimen.

* * * * *